US011123012B2

(12) United States Patent
Fridman et al.

(10) Patent No.: US 11,123,012 B2
(45) Date of Patent: Sep. 21, 2021

(54) UNDERWATER MEASUREMENT OF BIOELECTRIC SIGNALS

(71) Applicant: Quantum Applied Science and Research, Inc., San Diego, CA (US)

(72) Inventors: Igor V. Fridman, San Diego, CA (US); Robert Matthews, Escondido, CA (US)

(73) Assignee: Quantum Applied Science & Research, Inc., San Diego, CA (US)

( * ) Notice: Subject to any disclaimer, the term of this patent is extended or adjusted under 35 U.S.C. 154(b) by 117 days.

(21) Appl. No.: 15/576,878

(22) PCT Filed: May 27, 2016

(86) PCT No.: PCT/US2016/034671
§ 371 (c)(1),
(2) Date: Nov. 27, 2017

(87) PCT Pub. No.: WO2016/191687
PCT Pub. Date: Dec. 1, 2016

(65) Prior Publication Data
US 2018/0146923 A1 May 31, 2018

Related U.S. Application Data

(60) Provisional application No. 62/167,059, filed on May 27, 2015.

(51) Int. Cl.
*A61B 5/25* (2021.01)
*A61B 5/00* (2006.01)
(Continued)

(52) U.S. Cl.
CPC .......... *A61B 5/6804* (2013.01); *A61B 5/0205* (2013.01); *A61B 5/25* (2021.01);
(Continued)

(58) Field of Classification Search
CPC ...... A61B 2562/0214; A61B 2562/182; A61B 5/0205; A61B 5/0408; A61B 5/04085;
(Continued)

(56) References Cited

U.S. PATENT DOCUMENTS 3,707,959 A * 1/1973 Wilton-Davies ....... A61B 5/366
600/516
4,681,118 A * 7/1987 Asai ..................... A61B 5/0006
600/390
(Continued)

FOREIGN PATENT DOCUMENTS

WO 2006/000345 1/2006

OTHER PUBLICATIONS

Lee et al. "Flexible capacitive electrodes for minimizing motion artifacts in ambulatory electrocardiograms." *Sensors* 14, No. 8 (2014): 14732-14743.

*Primary Examiner* — Eun Hwa Kim
*Assistant Examiner* — Rachel A. Vierra
(74) *Attorney, Agent, or Firm* — Diederiks & Whitelaw, PLC.

(57) ABSTRACT

A system and method of measuring bioelectric signals generated by an individual, inclusive of humans or other living organisms, comprises a plurality of sensors, at least one of the plurality of sensors being constituted by a capacitive-type sensor. Sensor has an associated insulated layer of material preventing the conduction of direct current between an electrode and individual, wherein a bioelectric signal of individual can be measured underwater.

22 Claims, 6 Drawing Sheets

(51) Int. Cl.
- *A61B 5/282* (2021.01)
- *A61B 5/291* (2021.01)
- *A61B 5/296* (2021.01)
- *A61B 5/398* (2021.01)
- *A61B 5/277* (2021.01)
- *A61B 5/0205* (2006.01)
- *B63C 11/12* (2006.01)
- *G01D 5/24* (2006.01)
- *A61B 5/28* (2021.01)
- *B63C 11/06* (2006.01)
- *B63C 11/24* (2006.01)
- *B63C 11/04* (2006.01)

(52) U.S. Cl.
CPC .............. *A61B 5/277* (2021.01); *A61B 5/282* (2021.01); *A61B 5/291* (2021.01); *A61B 5/296* (2021.01); *A61B 5/398* (2021.01); *B63C 11/12* (2013.01); *G01D 5/24* (2013.01); *A61B 5/28* (2021.01); *A61B 2503/10* (2013.01); *A61B 2562/0214* (2013.01); *A61B 2562/182* (2013.01); *B63C 11/06* (2013.01); *B63C 11/24* (2013.01); *B63C 2011/043* (2013.01); *B63C 2011/046* (2013.01)

(58) Field of Classification Search
CPC ... A61B 5/0478; A61B 5/0492; A61B 5/0496; A61B 5/6804; B63C 11/06; B63C 11/12; B63C 11/24; B63C 2011/043; B63C 2011/046; G01D 5/24
See application file for complete search history.

(56) References Cited

U.S. PATENT DOCUMENTS

| | | | |
|---|---|---|---|
| 6,411,108 B1 | 6/2002 | Douglas et al. | |
| 6,445,940 B1* | 9/2002 | Gevins | A61B 5/0478 600/382 |
| 6,551,252 B2 | 4/2003 | Sackner et al. | |
| 6,580,943 B2* | 6/2003 | Nissila | A61B 5/0006 600/372 |
| 6,686,800 B2 | 2/2004 | Krupka | |
| 6,961,601 B2* | 11/2005 | Matthews | A61B 5/0408 600/372 |
| 7,088,175 B2 | 8/2006 | Krupka | |
| 7,141,987 B2 | 11/2006 | Hibbs et al. | |
| 7,173,437 B2 | 2/2007 | Hervieux et al. | |
| 7,245,956 B2 | 7/2007 | Matthews et al. | |
| 7,518,443 B2 | 4/2009 | Matthews | |
| 8,054,176 B2 | 11/2011 | Karjalainen | |
| 8,773,146 B1 | 7/2014 | Hills et al. | |
| 8,914,122 B2 | 12/2014 | Simon et al. | |
| 9,439,599 B2 | 9/2016 | Thompson et al. | |
| 2004/0073104 A1* | 4/2004 | Brun del Re | A61B 5/6805 600/372 |
| 2006/0069320 A1 | 3/2006 | Wolff et al. | |
| 2008/0246485 A1 | 10/2008 | Hibbs et al. | |
| 2009/0264776 A1* | 10/2009 | Vardy | A61B 5/0295 600/506 |
| 2010/0148789 A1 | 6/2010 | Hibbs et al. | |
| 2012/0056631 A1* | 3/2012 | Feddes | A61B 5/25 324/686 |
| 2014/0073896 A1* | 3/2014 | Hyatt | A61N 1/048 600/391 |
| 2014/0088397 A1 | 3/2014 | Chon et al. | |
| 2014/0361777 A1 | 12/2014 | Marsala et al. | |
| 2015/0366504 A1 | 12/2015 | Connor | |
| 2016/0029911 A1 | 2/2016 | Lee | |

* cited by examiner

UNDERWATER MEASUREMENT OF BIOELECTRIC SIGNALS

CROSS-REFERENCE TO RELATED APPLICATIONS

The present application represents the U.S. National Phase of International Application number PCT/US2016/034671, which was filed on May 27, 2016, which claims the benefit of U.S. Provisional Application Ser. No. 62/167,059, which was filed on May 27, 2015 and titled "Underwater Measurement of Bioelectric Signals". The entire content of this application is incorporated herein by reference.

BACKGROUND OF THE INVENTION

The present invention relates to the art of measuring bioelectric signals using sensor systems incorporating at least one capacitive-type electric sensor, with that sensor being at least partially underwater.

It is widely known that electric potentials and fields are developed in free space from many different sources. For example, organs in the human body, including the heart and brain, produce electric fields throughout the body and in the space outside the body. For a variety of reasons, it is often desirable to measure these electric fields, such as in performing an electrocardiogram (ECG). Indeed, the measurement of bioelectric signals can provide critical information about the physiological status and health of an individual. Accordingly, such measurements are widely used in monitoring, evaluating, diagnosing and caring for patients. Prior methods of measuring electric potentials associated with human or animal subjects involve securing gel-coated electrodes directly to the skin or scalp or inserting electrodes into the body.

More specifically, electrodes that make a resistive (i.e., Ohmic) electrical contact have been predominantly employed in connection with measuring electric potentials produced by animals and human beings. The disadvantages of such resistive electrodes include discomfort for the subject, the requirement for conducting gels and/or adhesives, difficulty in establishing good electrical contact because of differing physical attributes of the subject (hair, skin properties, etc.), and the degradation in resistive coupling quality over time, among others. These limitations have created a significant barrier to the use of resistive electrodes over extended periods of time and/or when convenience of use is paramount. Resistive electrodes are especially ineffective when submersed in water. Due to the conducting properties of the water, whether it be fresh water, chlorinated water or seawater, resistive electrodes require extensive waterproofing of the electrode and skin-to-electrode interface to provide useful measurements.

Another type of sensor that has been proposed in measuring biopotentials is a capacitive sensor. Early capacitive sensors required a high mutual capacitance to the body, thereby requiring the sensor to also touch the skin of the patient. The electrodes associated with these types of sensors are strongly affected by lift-off from the skin, particularly since the capacitive sensors are not used with conducting gels. As a result, early capacitive sensors were not found to provide any meaningful benefits and were not generally adopted over resistive sensors. However, advances in electronic amplifiers and new circuit techniques have made possible a new class of capacitive sensor that can measure electrical potentials, when coupling to a source, on the order of 1 pF or less. This capability makes possible the measurement of bioelectric signals with electrodes that do not need a high capacitance to the subject, thereby enabling the electrodes to be used without being in intimate electrical and/or physical contact with the subject. Such capacitive-type sensors and sensing systems have been previously disclosed.

There currently exists a need for bioelectric signals to be measured in a noninvasive, convenient, unobtrusive and effective way on subjects that are at least partially underwater. To be useful, this measurement should commence with minimal setup or preparation time, and proceed with little or no intervention. Whereas current techniques require extensive waterproofing with waterproof membranes, adhesives, additional housings or the like, capacitive-type sensors disclosed herein enable measurements of bioelectric signals underwater without any additional waterproofing of the sensor and/or the skin-to-sensor interface.

SUMMARY OF THE INVENTION

The present invention is directed to a system and method of measuring bioelectric signals generated by an individual, inclusive of humans or other living organisms, while the individual is at least partially underwater. Non-limiting examples of other living organisms include marine mammals, fish, aquatic animals, aquatic plants, marine invertebrates, or the like.

In general, the system and method enable bioelectric signals to be collected through one or more sensors, at least one of which constitutes a capacitive-type sensor. More particularly, the system and method enable the measurement to be made while at least one of the capacitive-type sensors is at least partially underwater. The sensors can be carried by a holding device or garment that can be worn by the individual. The sensors are either in direct contact with the skin of the individual or are spaced from the skin by a gap containing a substance or material.

Preferably, one or more of the capacitive-type sensors are active and have an associated electrically insulated layer of material preventing the conduction of direct current. The capacitive-type sensors are preferably mounted in a harness or holding structure. In some embodiments, the system can include an injection electrode adapted to inject a current or voltage into the individual's body to generate the bioelectric signal as a resulting voltage in the individual.

The active capacitive-type sensor has an input electrode covered with an associated insulated layer of material preventing the conduction of direct current. In some embodiments, the sensor also has a first stage amplifier connected to the input electrode and a housing encasing the input electrode and a wire. In some embodiments, the housing is connected to a passive or active shield (e.g., ground or guard) for protecting the signal from electromagnetic interference.

The capacitive-type sensor requires little or no additional waterproofing of either its input electrode or the area immediately surrounding the sensor. Furthermore, a capacitive-type sensor can function properly even if the sensor is in partial contact with water or is underwater or the insulating layer covering the input electrode comes into direct contact with water. While this application describes capacitive-type sensors embedded or otherwise integrated into a holding device worn by or mounted on an individual, regardless of the particular implementation, the method of the present invention enables bioelectric signals to be continuously measured underwater in a noninvasive, convenient, unobtrusive and effective way, with little setup or intervention.

Figure 3A:
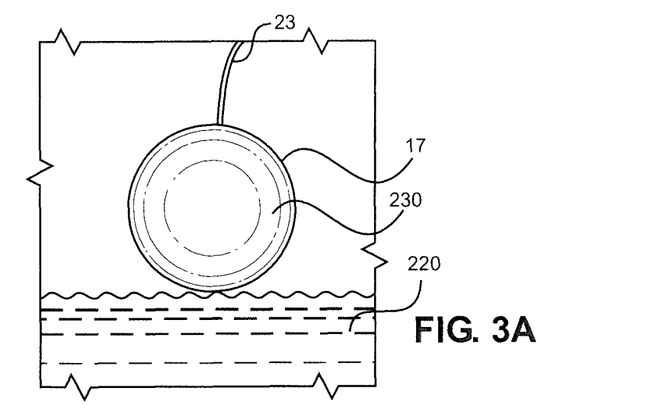
FIG. 3A shows a capacitive-type sensor whose housing is in contact with water.
Figure 3B:
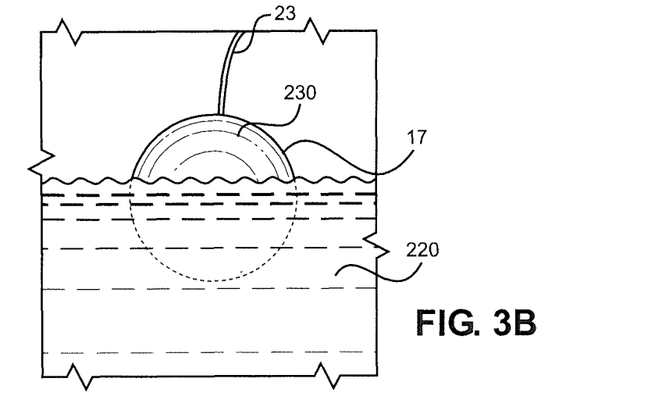
FIG. 3B shows a capacitive-type sensor whose housing is partially submerged in water, also termed partially underwater in this application.
Figure 3C:
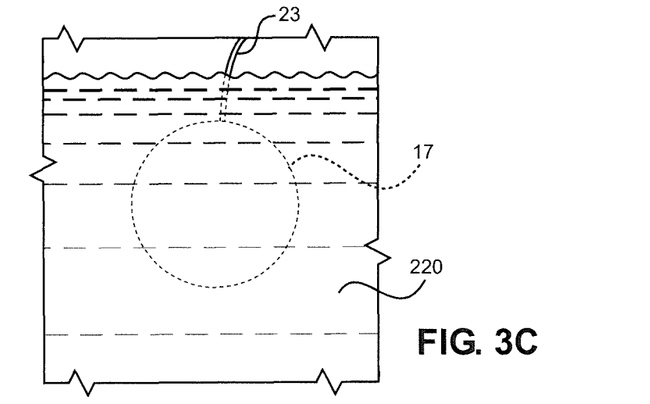
FIG. 3C shows a capacitive-type sensor whose housing is fully submerged in water, also termed completely underwater in this application, with the sensor cable at least partially submerged.
Figure 4A:
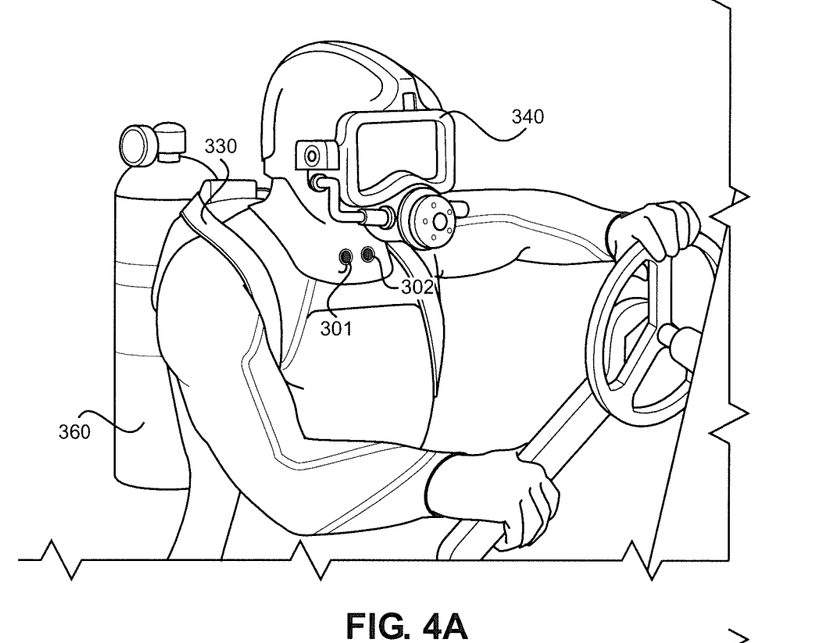
FIGS. 4A-4D show a wet suit, dive mask and other garments incorporating capacitive-type sensors on the torso and other areas of the individual.
Figure 4B:
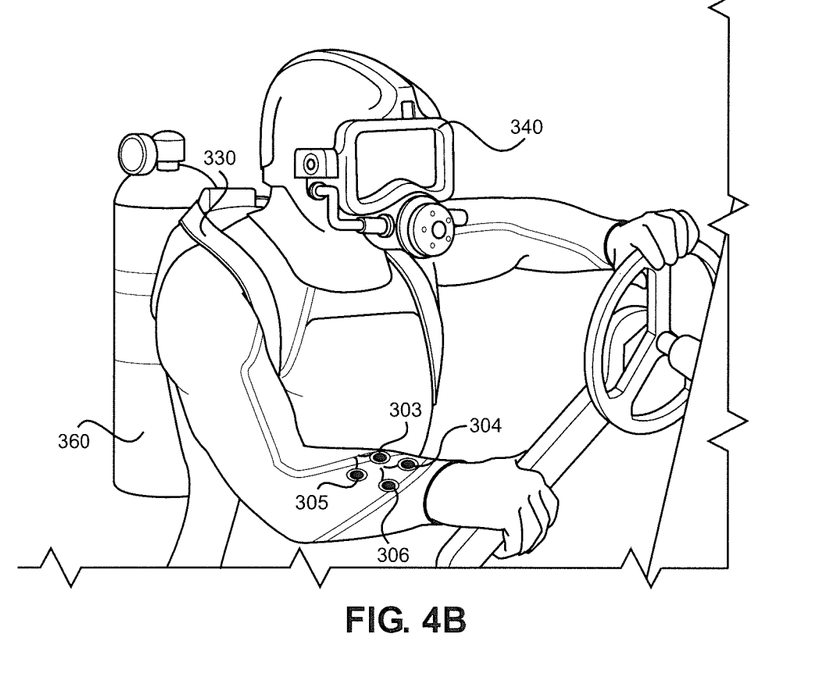
Figure 4C:
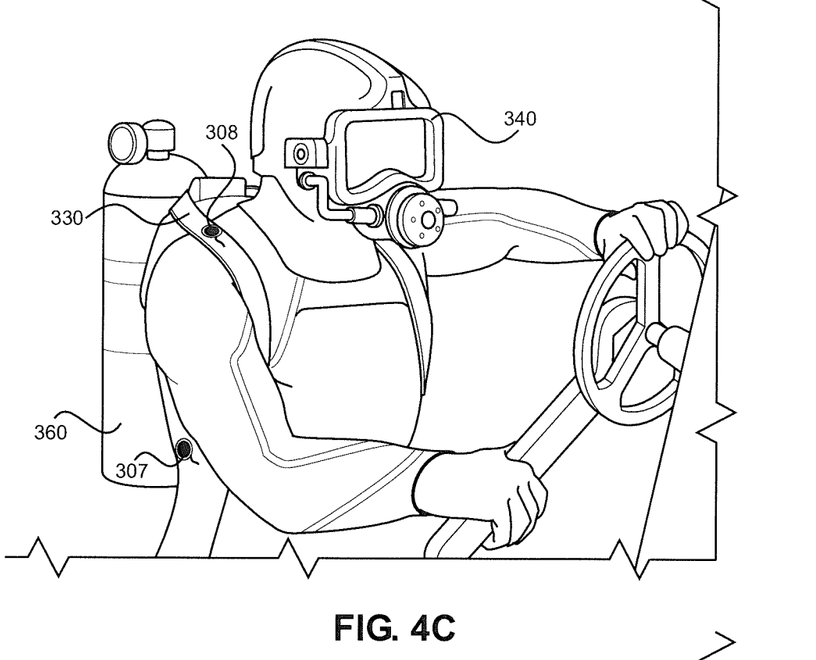
Figure 4D:
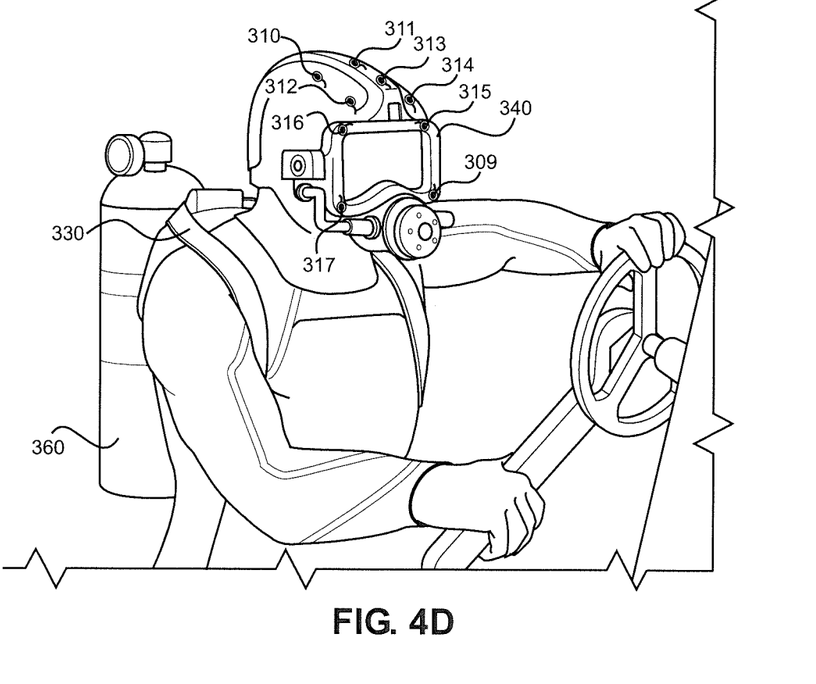

Another embodiment is directed to a method for measuring bioelectric signals underwater, the method comprising placement of at least two sensors on an individual, wherein at least one of the sensors is constituted by a capacitive-type sensor. The method further comprises measurement of the signals of the sensors while at least one of the capacitive-type sensors is at least partially underwater. In some embodiments, by partially underwater, it is meant that at least one of the sensors and the sensor housing is partially submerged in water. An example of this embodiment is shown in FIG. 3B. In certain embodiments, by partially underwater, it is meant that there is at least some water present between the individual and at least one of the sensors and the sensor housing is partially submerged in water. In some embodiments, at least one of the capacitive-type sensors is completely underwater. In some embodiments, by completely underwater, it is meant that the sensor housing is completely submerged in water. An example of this embodiment is shown in FIG. 3C. In some embodiments, by completely underwater, it is meant that the sensor housing is completely submerged in water and there is at least some water present between the individual and at least one of the sensors.

The capacitive-type sensor is preferably an active sensor. The placement of the at least two sensors involves placing the insulating layer of the sensors in direct physical contact with the skin of the individual. Alternatively, the placement of the at least two sensors involves placing the sensors at a distance to the individual, forming a gap between the insulating layer and the skin. In certain embodiments, the gap can comprise vacuum, air, water, hair, textile, cloth, foam, rubber, plastic, fiber, or combinations thereof.

In some embodiments, the placement of at least two sensors involves attaching the sensors to the individual using a holding device. The holding device can be a clothing garment, a wet suit, a dry suit, a harness, an elastic strap, a diving helmet, a diving mask, a head covering, a device worn around the wrist, a backpack, SCUBA equipment, SCUBA gas tank, closed circuit rebreather, or combinations thereof.

The capacitive-type sensor preferably has at least one associated insulating layer limiting the conduction of direct current below 1 pA. The measurement of the signals is performed while at least one of the capacitive-type sensors is in at least partial contact with water, while at least one of the capacitive-type sensors is partially under the water level or while at least one of the capacitive-type sensors is completely underwater.

In certain embodiments, the measurement of the signals is performed while at least one of the capacitive-type sensors is at least partially covered with mechanical or structural enclosures that protect the sensor and/or the skin-to-sensor interface from water or while at least one of the capacitive-type sensors is at least partially covered with a hydrophobic material or coating.

In some embodiments, the bioelectric signal is measured from a living organism such as a human being, aquatic animal, aquatic plant, marine mammal or fish. The measured bioelectric signals can comprise signals generated by any organs of the living organism such as the internal organs of the living organism, the cardiac system of the living organism, the nervous system of the living organism, the muscles of the living organism, including but not limited to the facial, laryngeal, forearm or thoracic muscles, or the eyes of the living organism.

The measured bioelectric signals comprise an electrocardiogram (ECG), an electroencephalogram (EEG), an electrooculogram (EOG), an electromyogram (EMG) and combinations thereof. In certain embodiments, as part of an impedance measurement, the measured bioelectric signals can also comprise the voltage produced by an excitation injected into the individual's body. The impedance measurement is used in the determination or calculation of body composition, respiratory function, Body Impedance Analysis (BIA), Body Mass Index, Multi-Frequency Body Impedance Analysis (MF-BIA), Extra Cellular Water (ECW), Intra Cellular Water (ICW) or the like and combinations thereof.

The at least two sensors includes a first sensor and second sensor. The first sensor can be a capacitive-type sensor. The second sensor can be another capacitive-type sensor, a non-capacitive sensor, an active or passive reference sensor, or a common-mode follower sensor.

Yet another embodiment includes a sensor system for measuring bioelectrical signals of an individual comprising a plurality of sensors, at least one of the plurality of sensors being constituted by a capacitive-type sensor, wherein the bioelectric signal of an individual can be measured underwater. Preferably the at least one of the capacitive-type sensors is active. The at least one of the capacitive-type sensors has an associated insulated layer of material preventing the conduction of direct current. The at least one of the capacitive-type sensors is in contact with water or completely underwater or submerged.

In certain embodiments, the plurality of capacitive-type sensors is mounted in a harness or holding structure, the plurality of capacitive-type sensors is embedded into a wet or dry diving suit or the plurality of capacitive-type sensors is embedded into a holding device worn by, attached to, or nearby the individual.

In certain embodiments, the placement of the at least two sensors involves placing the insulating layer of the sensors in direct physical contact with the skin of the individual. Alternatively, the placement of the at least two sensors involves placing the sensors at a distance from the individual, forming a gap between the insulating layer and the skin. In some embodiments, the plurality of electrical sensors is arranged at specified locations.

Additional objects, features and advantages of the present invention will become more readily apparent from the following detailed description of a preferred embodiment when taken in conjunction with the drawings wherein like reference numerals refer to corresponding parts in the several views.

DETAILED DESCRIPTION OF THE PREFERRED EMBODIMENTS

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

In the description which follows, like parts may be marked throughout the specification and drawing with the same reference numerals. The foregoing description of the figures is provided for a more complete understanding of the drawings. It should be understood, however, that the embodiments are not limited to the precise arrangements and configurations shown. Although the design and use of various embodiments are discussed in detail below, it should be appreciated that the present invention provides many inventive concepts that may be embodied in a wide variety of contexts. The specific aspects and embodiments discussed herein are merely illustrative of ways to make and use the invention and do not limit the scope of the invention. It would be impossible or impractical to include all of the possible embodiments and contexts of the invention in this disclosure. Upon reading this disclosure, many alternative embodiments of the present invention will be apparent to persons of ordinary skill in the art.

Figure 1:
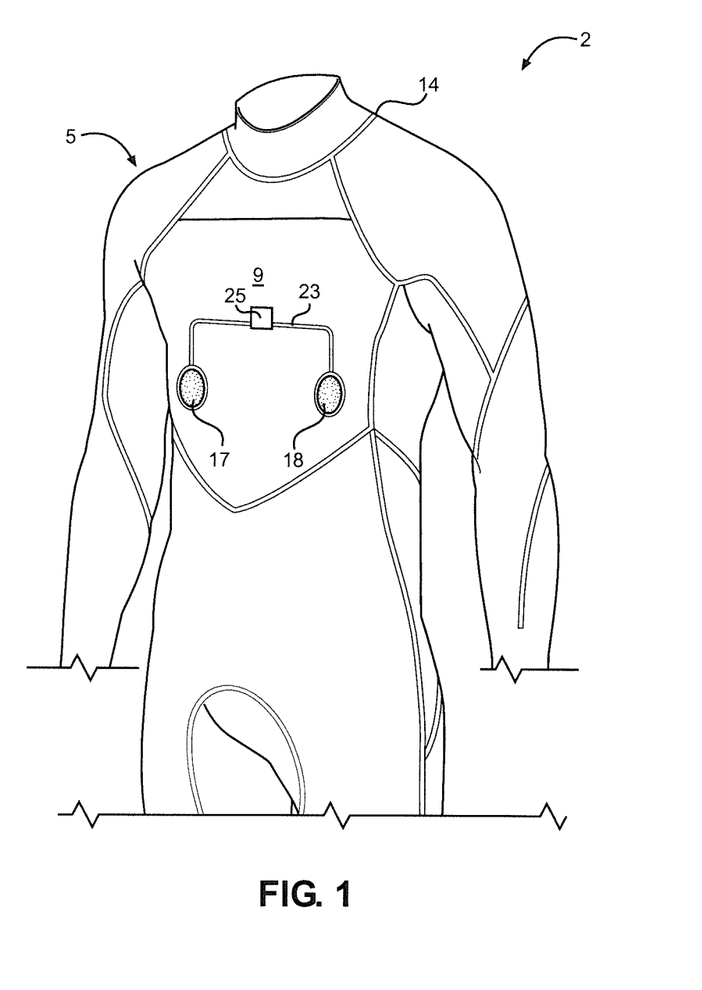
FIG. 1 shows a capacitive-type sensor, mounted on an article of clothing, measuring the electric field of the individual.

With initial reference to FIG. 1, a sensor system constructed in accordance with the present invention is generally indicated at 2. In general, sensor system 2 functions to measure biopotentials of an individual 5. As shown, individual 5 includes a chest 9. Individual 5 is wearing a holding device 14, such as a wet suit, which forms part of sensor system 2. More specifically, sensor system 2 includes holding device 14 having embedded, or otherwise integrated, sensors 17 and 18. In accordance with the invention, at least first sensor 17 constitutes a capacitive-type sensor. In the most preferred embodiment, both sensors 17 and 18 are active capacitive-type sensors. In another embodiment, sensor 18 includes electrodes configured to inject a current into individual 5. In yet another embodiment, sensor 18 constitutes a common-mode follower sensor, grounding electrode or the like.

In the embodiment shown, holding device 14 is a wetsuit. However, other types of garments or articles worn by an individual while in water could be employed. Even though only sensors 17 and 18 are shown, additional sensors may be employed. Also, while sensors 17 and 18 are shown as having a tethered connection (via a cable 23), other connections could be used. Additional information regarding the connection of sensors 17 and 18 to a control unit (or electronics module) 25 and the operation of control unit 25 is disclosed in U.S. Pat. Nos. 7,173,437 and 7,245,956, which are incorporated herein by reference.

Figures 2A, 2B:
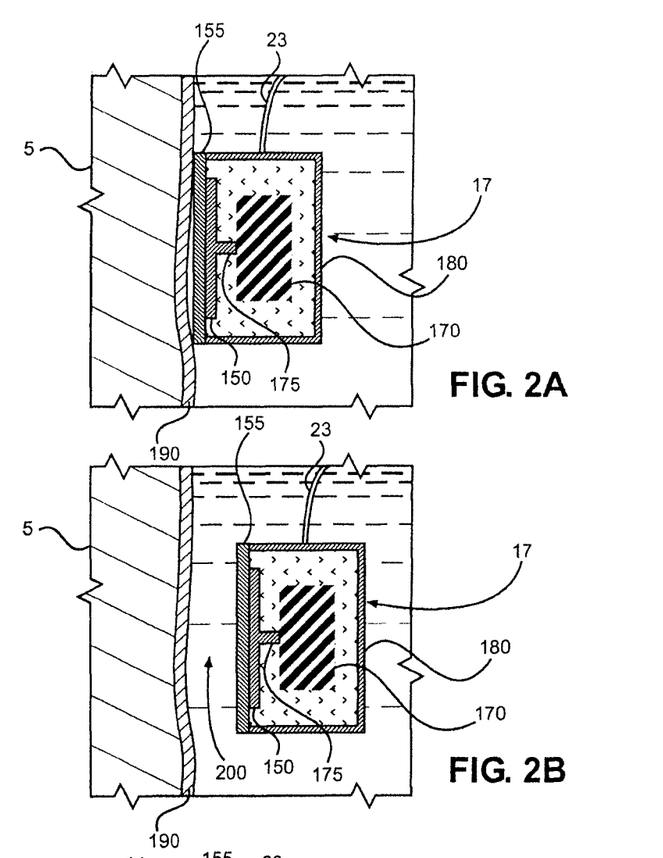
FIG. 2A shows a cross-sectional drawing of the capacitive-type sensor of FIG. 1.
FIG. 2B shows a cross-sectional drawing of a capacitive-type sensor measuring the electric field of the individual, with the insulating layer of the sensor at a distance from the skin of the individual.

As noted above, at least one sensor of sensor system 2 constitutes a capacitive-type sensor. With reference to FIG. 2A, capacitive-type sensor 17 measures the electric field produced by individual 5. Capacitive-type sensor 17 contains an input electrode 150. Input electrode 150 is a passive sensing element whose charge, current or voltage is measured and which generally has electrically conductive properties. Capacitive-type sensor 17 further includes an insulating layer 155, which generally has electrically insulating properties. Insulating layer 155 covers input electrode 150 so as to ensure that little or no direct electrical current flows between the sensor's input electrode 150 and individual 5. More specifically, if a constant voltage difference of 1 mV were applied between individual 5 and input electrode 150, the direct electrical current between individual 5 and input electrode 150 would be approximately less than 1 aA (atto-Ampere), less than 500 aA, less than 1 fA, less than 10 fA, less than 50 fA, less than 100 fA, less than 200 fA, less than 300 fA, less than 500 fA, less than 750 fA, less than 1 pA, less than 10 pA, less than 50 pA, less than 100 pA, less than 200 pA, less than 300 pA, less than 500 pA, less than 750 pA, less than 1 nA, less than 10 nA, less than 50 nA, less than 100 nA, less than 200 nA, less than 300 nA, less than 500 nA, less than 750 nA, less than 1 µA, less than 10 µA, less than 100 µA, or less than 1 mA. Even more specifically, capacitive-type sensor 17 has a capacitance between input electrode 150 and the individual's skin 190, skin being defined herein as the outermost natural surface of the individual, of approximately less than less than 1 fF (femto-Farad), less than 10 fF, less than 50 fF, less than 100 fF, less than 200 fF, less than 300 fF, less than 500 fF, less than 750 fF, less than 1 pF, less than 2 pF, less than 5 pF, less than 10 pF, less than 30 pF, less than 50 pF, less than 70 pF, less than 100 pF, less than 130 pF, less than 150 pF, less than 180 pF, less than 200 pF, less than 250 pF, less than 300 pF, less than 400 pF, less than 500 pF, less than 750 pF, less than 1 nF, less than 2 nF, less than 5 nF, less than 10 nF, less than 20 nF, less than 50 nF, less than 100 nF, less than 200 nF, less than 500 nF, or less than 1 µF.

Figure 2C:
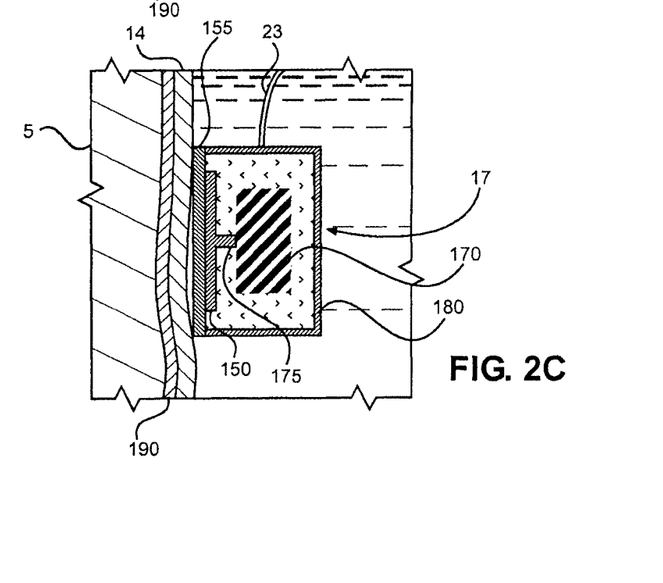
FIG. 2C shows a cross-sectional drawing of a capacitive-type sensor measuring the electric field of the individual, with a material between the insulating layer of the sensor and the skin of the individual.

With reference to FIGS. 2A-2C depicting various ways of applying capacitive-type sensor 17 to individual 5, it should be readily understood that the disclosed embodiments are merely exemplary of the invention that may be embodied in various and alternative forms. For example, individual 5 shown in FIGS. 2A-2C is preferably any living organism, non-limiting examples of which are human beings, such as swimmers, athletes, underwater divers, medical patients, warfighters or the like, or other living organisms such as marine mammals, fish, aquatic animals, aquatic plants, marine invertebrates, or the like. In some embodiments of the capacitive-type sensor, there may be additional mechanical or electrical structures such as passive or driven ground planes, additional shielding layers, additional wiring and/or circuitry, or additional electrical components such as operational amplifiers, transistors, resistors, capacitors or the like. In accordance with the invention, input electrode 150 is made of a plate, film, foil, coating, fabric, rubber, plastic or the like and combinations thereof. Non-limiting examples of input electrode 150 are a metallic plate, foil or trace fabricated using printed circuit board techniques. Non-limiting examples of the shape and size of input electrode 150 include a flat disc measuring 0.1 mm thick and 1.5 cm in diameter, a disc with grooves or indentations, or a comb-like structure with deep grooves. In accordance with the invention, insulating layer 155 is made of a plate, film, foil, coating, oxide layer, passivation layer, anodization layer, rubber, plastic, polymer, composite, ceramic or the like and combinations thereof. Non-limiting examples of insulating layer 155 are a rigid plastic sheet, a rubber coating, a lamination layer, or an anodization, oxidation or passivation layer deposited on input electrode 150. Non-limiting examples of capacitive-type and/or capacitive-like sensors include sensors developed by QUASAR, Inc. described in U.S. Pat. Nos. 7,088,175, 6,961,601, 6,686,800, 7,141,987 and 7,518,443, which are incorporated herein by reference.

In accordance with one embodiment of the system, the capacitive-type sensor of sensor system 2 constitutes a passive sensor, wherein a first stage amplifier is located a substantial distance away from the input electrode. Specifically, the lesser of the length of the electrode wire and the distance between the input electrode and the first stage amplifier is greater than 300 mm. For example, with reference to FIG. 1, the input electrode could be placed in sensor 18 and the first stage amplifier could be placed near electronics module 25.

In accordance with a preferred embodiment of the system, the capacitive-type sensor constitutes an active sensor. With reference to FIG. 2A, an active sensor 17 includes a first stage amplifier 170 located near input electrode 150 and connected to input electrode 150 with an electrode wire 175. Active sensor 17 further comprises a housing 180 enclosing input electrode 150, electrode wire 175 and first stage amplifier 170. The lesser of the length of electrode wire 175 and the distance between input electrode 150 and first stage amplifier 170 is less than 0.1 mm, 0.2 mm, 0.5 mm, 0.7 mm, 1 mm, 2 mm, 5 mm, 7 mm, 10 mm, 12 mm, 15 mm, 17 mm, 20 mm, 30 mm, 50 mm, 10 cm, 20 cm, 50 cm, 70 cm, 100 cm, 150 cm, 200 cm or 300 cm. A non-limiting example of first stage amplifier 170 is an operational or instrumentation amplifier having sufficiently high input impedance and low input bias current to effectively buffer or amplify the signal sensed by input electrode 150. Non-limiting examples of electrode wire 175 are a conductive wire, a trace fabricated using printed circuit board techniques, an electrical connector, a snap-type connector, a magnetically-coupled connector or the like and combinations thereof. Non-limiting examples of housing 180 are enclosures having electrically insulating or conductive properties, or combinations thereof. An insulating housing can be made from a material such as plastic or the like. A conductive housing can be made from a metallic material and electrically connected to a ground, passive or driven shield or guard voltage, or any other voltage. In another example, a housing is made from insulating plastic having a conductive coating applied to the inside. It should be readily understood that these examples of the components of an active sensor do not limit the specific implementation of such sensor, which may be constructed in alternate forms or have additional internal components, for example as disclosed in U.S. Pat. Nos. 6,686,800, 7,088,175 and 6,961,601, which are incorporated herein by reference.

Active sensor 17 has the following advantages over a passive sensor. First, encasing electrode wire 175 and first stage amplifier 170 in housing 180 that is connected to a ground, guard or other voltage shields these elements from electromagnetic interference from unwanted external sources. While a passive sensor may be used with an electrode wire that is encased in a shielded cable, the relatively long length of the electrode wire makes it nevertheless susceptible to either external electromagnetic interference or triboelectric charge generated between the electrode wire and its insulation. Second, the relatively long length of the electrode wire in the passive sensor creates a stray capacitance, on the order of 5 pF or higher, between the electrode wire and circuit elements such as ground, parts of the first stage amplifier or the like. This stray capacitance can make the sensor unstable in some operating conditions and reduces its sensitivity. Compensating for the stray capacitance using a driven shield can improve sensitivity but invariably increases sensor noise. Third, since this stray capacitance is difficult to control when fabricating multiple sensors, it can accentuate differences in the sensitivities of a pair or sensors whose outputs are differenced to produce a signal. This reduces the pair's common-mode rejection and makes the difference signal susceptible to motion or interference artifacts.

In accordance with one embodiment of the system, capacitive-type sensor 17 is in direct physical contact with the individual's skin 190. With reference to FIG. 2B and in accordance with another embodiment of the system, capacitive-type sensor 17 can also be held at a distance from skin 190, forming a gap 200 between skin 190 and insulating layer 155. Gap 200 can be filled by a medium or material such as vacuum, air, water, hair, textile, cloth, foam, rubber, plastic, fiber, or the like and combinations thereof. With reference to FIG. 2C and in accordance with yet another embodiment of the system, the material in gap 200 can be part of a garment or equipment worn by the individual. Specifically, gap 200 is shown filled by part of holding device 14, which may be made of textile, cloth, foam, rubber, plastic, fiber, or the like and combinations thereof and is used to attach sensor 17 to individual 5. Sensor function is not significantly altered by the properties and composition of the medium or material inside gap 200, such properties including, for example, electrical conductivity, triboelectric properties, dielectric properties, porosity, hydrophobicity, flexibility, strength and the like. The distance between insulating layer 155 and skin 190 is approximately less than 100 nm (nano-meter), less than 1 μm, less than 10 μm, less than 100 μm, less than 200 μm, less than 500 μm, less than 700 μm, less than 1 mm, less than 2 mm, less than 3 mm, less than 5 mm, less than 7 mm, less than 10 mm, or less than 20 mm.

In accordance with the invention, the system and method can be used to measure bioelectric signals while at least one of the capacitive-type sensors is at least partially underwater. With reference to FIGS. 3A-3C, any part of capacitive-type sensor 17 can be in contact with water 220, non-limiting examples of which include insulating layer 155, housing 180 or sensor cable 23. In one embodiment of system 2, individual 5, whose bioelectric signals are being measured, is submerged in water 220 with the water level being at least high enough to be in contact with capacitive-type sensor 17, as depicted in FIG. 3A. In a preferred embodiment, the water level is at least high enough to at least partially submerge capacitive-type sensor 17 underwater, as depicted in FIG. 3B. In the most preferred embodiment, the water level is high enough to fully submerge capacitive-type sensor 17 underwater, as depicted in FIG. 3C. In another embodiment, any part of capacitive-type sensor 17 can be underwater but not in direct contact with water. This is accomplished by at least partially enclosing insulating layer 155, housing 180 or sensor cable 23 in a mechanical structure or hydrophobic material or coating (generically shown and labeled 230) that prevents exposure thereof to the surrounding water. The system and method function without regard for water properties and composition, inclusive of conductivity, dielectric properties, temperature, pressure, salinity, chlorine content, particulate content, dissolved matter content or the like.

With reference to FIG. 4A-4D and in accordance with one embodiment of the system, sensors 301-317 are incorporated into a holding device worn by an individual. Non-limiting examples of sensor locations include a clothing garment, a wet suit, a dry suit, a harness 330, an elastic strap, a diving helmet or mask 340, a head covering, a device worn around the wrist, a backpack, self-contained underwater breathing apparatus (SCUBA) equipment, a SCUBA gas tank 360, a closed circuit rebreather, or the like.

In accordance with another embodiment of the system (not shown), sensors 17, 18, 301-317 can be mounted on fish or marine mammals by being incorporated into a holding device around the individual's torso, head, extremities or the like or combinations thereof. In accordance with another embodiment of the system (not shown), sensors 17, 18, 301-317 are attached to the individual without the use of a holding device and are held in place using adhesive, suction or the like.

The holding device preferably holds a sensor or a plurality of sensors at predetermined locations, non-limiting examples of which are standard measurement positions, an array of positions or the like. The holding device can also allow the sensor or a plurality of sensors to be freely positioned depending on the application. The holding device can be worn directly on the skin of the individual or on top of a garment or equipment worn by the individual. The system uses sensors that are placed in the region where the bioelectric signal of interest is to be measured. Non-limiting examples of sensor locations are the front or back of the torso of the individual or the abdomen, shoulder, neck, head, face, extremities, arms, fingers, palms, fins, roots, or the like.

The system and method are preferably employed to measure bioelectric signals, defined as electric signals produced by various organs of the individual, non-limiting examples of which are the heart, brain, muscle, eye, or the like. Non-limiting measurements made possible by the system include electrocardiogram (ECG), electroencephalogram (EEG), electrooculogram (EOG), electromyogram (EMG) or the like, or combinations thereof. In certain embodiments, these measurements span a range of frequencies from 0 to at least 10 MHz. In some embodiments, the lowest frequency is at least 0.0001 Hz, at least 0.001 Hz, at least 0.01 Hz, at least 0.05 Hz, at least 0.1 Hz, at least 0.5 Hz, at least 1 Hz, at least 2 Hz, at least 5 Hz, at least 10 Hz, at least 50 Hz, at least 100 Hz, at least 500 Hz or at least 1000 Hz. In certain embodiments, the highest frequency is at most 0.1 Hz, at most 1 Hz, at most 10 Hz, at most 20 Hz, at most 30 Hz, at most 50 Hz, at most 75 Hz, at most 90 Hz, at most 100 Hz, at most 130 Hz, at most 150 Hz, at most 200 Hz, at most 300 Hz, at most 500 Hz, at most 1 kHz, at most 2 kHz, at most 5 kHz, at most 10 kHz, at most 100 kHz, at most 1 MHz, or at most 10 MHz.

Non-limiting examples of the uses of measured ECG signals include: studies or monitoring of cardiac function; detection of health-related ailments such as arrhythmias and cardiac traumas; research of swimmer or diver health; research into hyperbaric exposures and associated diseases; development or modification of decompression algorithms; calculation of decompression stops; sports performance monitoring or enhancement; electrophysiology; pathoelectrophysiology; research into heart function; heart disorders; pharmacological drug development or the like. Measured ECG signals can also be used to derive information about the individual's respiration rate or waveform, or study or detect physiological health ailments such as injury, trauma, hypoxia, hyperoxia, asphyxia, or the like and combinations thereof. In certain embodiments, these ECG measurements span a range of frequencies from 0 to at least 1 kHz. In some embodiments, the lowest frequency is at least 0.0001 Hz, at least 0.001 Hz, at least 0.01 Hz, at least 0.05 Hz, at least 0.1 Hz, at least 0.5 Hz, at least 1 Hz, at least 2 Hz, at least 5 Hz, at least 10 Hz, at least 50 Hz, at least 100 Hz, at least 500 Hz or at least 1000 Hz. In certain embodiments, the highest frequency is at most 10 Hz, at most 20 Hz, at most 30 Hz, at most 50 Hz, at most 75 Hz, at most 90 Hz, at most 100 Hz, at most 130 Hz, at most 150 Hz, at most 200 Hz, at most 300 Hz, at most 500 Hz, or at most 1 kHz. In a preferred embodiment, ECG measurements span a frequency range between 0.05 Hz and 100 Hz.

Non-limiting examples of the uses of measured EEG signals include studies of cognitive function, cognitive performance, cognitive augmentation, individual's mood, cognitive state such as mental workload, fatigue or the like, as well as detection of neurological or physiological health ailments such as injury, trauma, high-pressure nervous syndrome, inert gas narcosis, hypoxia, hyperoxia or the like and combinations thereof. In certain embodiments, these EEG measurements span a range of frequencies from 0 Hz to at least 10 kHz. In certain embodiments, the lowest frequency is at least 0.0001 Hz, at least 0.001 Hz, at least 0.01 Hz, at least 0.05 Hz, at least 0.1 Hz, at least 0.5 Hz, at least 1 Hz, at least 2 Hz, or at least 10 Hz. In certain embodiments, the highest frequency is at most 20 Hz, at most 30 Hz, at most 50 Hz, at most 75 Hz, at most 90 Hz, at most 100 Hz, at most 130 Hz, at most 150 Hz, at most 200 Hz, at most 300 Hz, at most 500 Hz, at most 1 kHz, at most 2 kHz, at most 5 kHz, or at most 10 Hz. In a preferred embodiment, EEG measurements span a frequency range between 0.1 Hz and 100 Hz.

Non-limiting examples of the uses of measured EOG signals include recording eye or gaze position, recording eye or gaze movements, determining the health of the individual or the like and combinations thereof. In certain embodiments, these EOG measurements span a range of frequencies from 0 Hz to at least 1 kHz. In certain embodiments, the lowest frequency is at least 0.0001 Hz, at least 0.001 Hz, at least 0.01 Hz, at least 0.05 Hz, at least 0.1 Hz, at least 0.5 Hz, at least 1 Hz, at least 2 Hz, or at least 10 Hz. In certain embodiments, the highest frequency is at most 20 Hz, at most 30 Hz, at most 50 Hz, at most 75 Hz, at most 90 Hz, at most 100 Hz, at most 130 Hz, at most 150 Hz, at most 200 Hz, at most 300 Hz, at most 500 Hz, or at most 1 kHz. In a preferred embodiment, EOG measurements span a frequency range between 0.05 Hz and 100 Hz.

Non-limiting examples of the uses of measured EMG signals include studies or detection of physiological health ailments such as injury or trauma, muscle activation level, muscle recruitment, subvocalization, movement, or for biomechanical augmentation of the individual or the like and combinations thereof. In certain embodiments, these EMG measurements span a range of frequencies from 0 Hz to at least 10 kHz. In certain embodiments, the lowest frequency is at least 5 Hz, at least 10 Hz, at least 20 Hz, at least 30 Hz, at least 40 Hz, at least 50 Hz, at least 60 Hz, at least 75 Hz or at least 100 Hz. In certain embodiments, the highest frequency is at most 100 Hz, at most 130 Hz, at most 150 Hz, at most 200 Hz, at most 300 Hz, at most 500 Hz, at most 1 kHz, at most 2 kHz, at most 5 kHz, or at most 10 kHz. In a preferred embodiment, EMG measurements span a frequency range between 5 Hz and 1 kHz. EMG signals generally occur at frequencies above 5 Hz. On the other hand, motion and other artifacts occur predominantly at frequencies between 0.1 Hz and 5 Hz. Thus, filtering out low frequencies during EMG measurements effectively reduces artifacts without sacrificing signal. This makes EMG measurements less challenging to perform in practice than ECG, EOG or EEG. These latter measurements are more challenging because filtering out low frequencies to reduce artifacts would significantly alter the signals of interest, and is therefore often not an option.

With reference to EEG, EOG and EMG, the measured signals can further be used as a method of communication between individual 5 and an external device, computer system, or another individual, wherein specific electrical brain signals, eye or muscle movements or activations are interpreted as communications, commands or inputs to a device. The device is defined as capable of interpreting the measured signals and issuing or executing communications or actions as a response. Non-limiting examples of such a device include portable or wearable computers, dive watches, dive computers, dive equipment, communications equipment, unmanned or robotic vehicles or the like or combinations thereof. Non-limiting examples of such communication include clandestine communications between individuals with subvocal speech or muscle activations, brain-computer interfaces, control of an unmanned robotic system, or sending of commands to a computer or another system. Non-limiting examples of individuals using such a system include disabled persons, medical patients, athletes, warfighters or the like and combinations thereof.

The system and method can also be employed to measure body impedance, wherein the electrical response of the body to an excitation signal is measured. At least one sensor is used to inject an alternating voltage or current excitation into the body of individual 5, and at least one sensor is used to measure the resulting voltage produced by the excitation. Accordingly, a plurality of sensors is used to perform this measurement, with at least one of the sensors constituted by a capacitive-type sensor. A non-limiting example of the measurement scheme is a two-sensor configuration where one sensor injects the excitation and the second measures the voltage. The resulting signal can be used to calculate the impedance of the individual's body. Non-limiting examples of the uses of this impedance measurement include the determination or calculation of body composition, respiratory function, Body Impedance Analysis (BIA), Body Mass Index, Multi-Frequency Body Impedance Analysis (MF-BIA), Extra Cellular Water (ECW), Intra Cellular Water (ICW) or the like and combinations thereof. These measurements span a range of frequencies, with the lower bound being at most 0.001 Hz, at most 0.01 Hz, at most 0.05 Hz, at most 0.1 Hz, at most 0.5 Hz, at most 1 Hz, at most 2 Hz, or at most 10 Hz, and the upper bound being at least 20 Hz, at least 30 Hz, at least 50 Hz, at least 75 Hz, at least 90 Hz, at least 100 Hz, at least 130 Hz, at least 150 Hz, at least 200 Hz, at least 300 Hz, at least 500 Hz, at least 1 kHz, at least 2 kHz, at least 5 kHz, at least 10 kHz, at least 100 kHz, at least 1 MHz, or at least 10 MHz.

Figure 5:
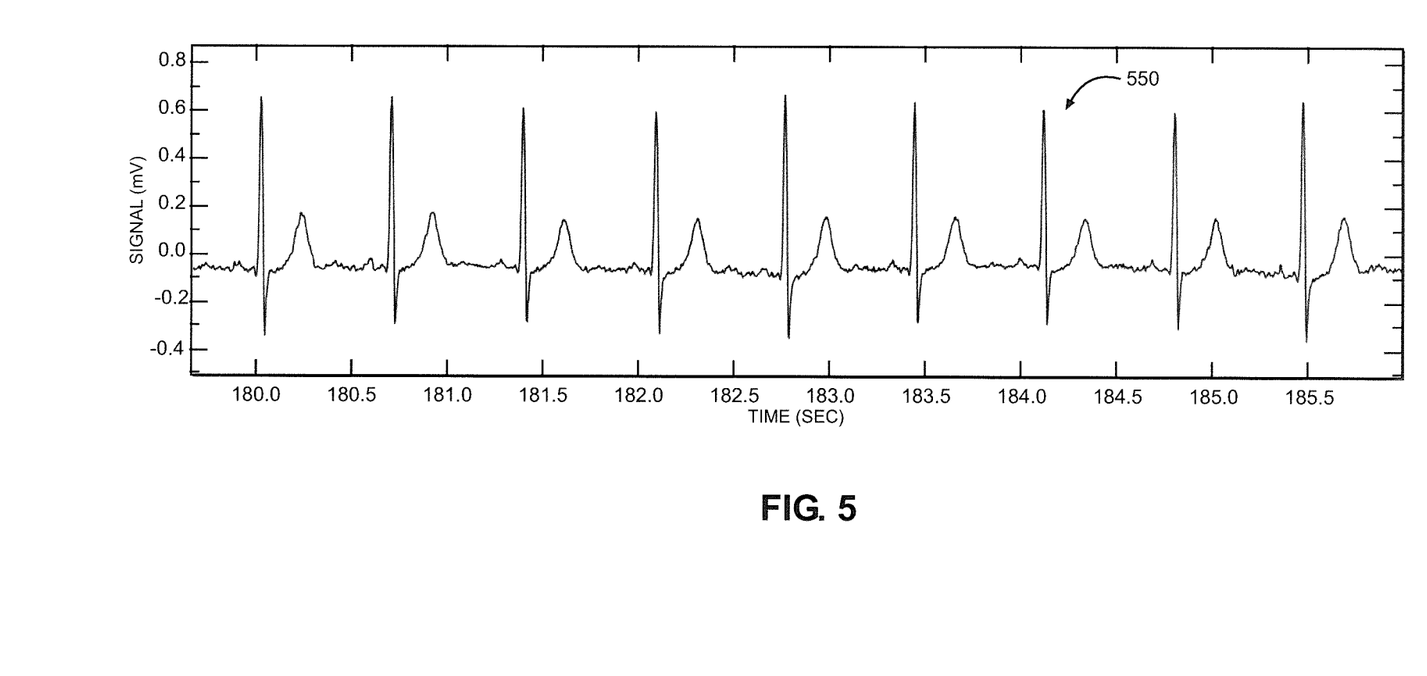
FIG. 5 shows a detailed view of the ECG signal while the sensors are submerged in seawater.

With reference to FIG. 5, the performance of the system is demonstrated. FIG. 5 depicts the difference in voltage measured between two capacitive-type sensors placed on the chest of a human individual, the signal exhibiting an ECG waveform 550. FIG. 5 shows a detailed view of a signal 550 while sensors 17, 18 are underwater, demonstrating that all parts of the ECG waveform are clearly distinguishable, including the P, Q, R, S and T waves.

Analog signals obtained by the sensors can be digitized and recorded by individual sensors or by an electronics module 25 worn by the individual, non-limiting examples of which include a device containing a microprocessor, a device containing storage media, a wrist-worn computer, a wrist-worn dive computer, or the like. The resulting measurements or data derived from them can be stored to local memory or transmitted wired, wirelessly, acoustically or through telemetric communication to another device located on the individual or remotely. The measurements or data derived from them can be output from the electronics module by means of a visual display, stored onto the cloud, viewed remotely, or the like and combinations thereof.

Although described with reference to preferred embodiments of the invention, it should be readily understood that the disclosed embodiments are merely exemplary of the invention that may be embodied in various and alternative forms. Furthermore, various changes and/or modifications can be made to the invention without departing from the spirit thereof. For example, the system and method is described as measuring bioelectric signals of an individual. However, the individual can be defined as any living organism, non-limiting examples of which are human beings, such as swimmers, athletes, underwater divers, medical patients, warfighters or the like, or other living organisms such as marine mammals, fish, aquatic animals, aquatic plants, marine invertebrates, or the like. Therefore, specific structural and functional details disclosed herein are not to be interpreted as limiting, but merely as a representative basis to variously employ the present invention for underwater measurements of bioelectric signals.

We claim:

1. A method for measuring bioelectric signals underwater comprising:
    placing two sensors on an individual, wherein each sensor of the two sensors is a capacitive-type sensor having an input electrode, a first stage amplifier connected to the input electrode, a wire and an associated insulating layer of material, wherein placing the two capacitive-type sensors involves placing each capacitive-type sensor at a distance from the individual and forming a respective gap between the associated insulating layer of material and skin of the individual so as to prevent conduction of direct current between the skin of the individual and each capacitive-type sensor;
    preventing the conduction of the direct current by covering each input electrode with the associated insulated layer of material;
    encasing the input electrode in a conductive housing;
    driving a guard voltage to the conductive housing to protect the input electrode from electromagnetic interference; and
    measuring the bioelectric signals with the two capacitive-type sensors while at least one of the two capacitive-type sensors is at least partially underwater and while there can be at least some water present between the individual's skin and the associated insulating layer of at least one of the two capacitive-type sensors wherein the guard voltage protects the bioelectric signals from electromagnetic interference.

2. The method according to claim 1, wherein measuring the bioelectric signals while at least one of the two capacitive-type sensors is at least partially underwater includes measuring the bioelectric signals while there is at least some water present between the individual's skin and each capacitive-type sensor.

3. The method according to claim 1, wherein at least one of the capacitive-type sensors is an active sensor.

4. The method according to claim 1, further comprising filling the respective gap with vacuum, air, water, hair, textile, cloth, foam, rubber, plastic, fiber or a combination thereof.

5. The method according to claim 1, wherein placing the two capacitive-type sensors includes mounting the capacitive-type sensors on a holding device comprising a garment, a wet suit, a dry suit, a harness, an elastic strap, a diving helmet, a diving mask, a head covering, a device worn around the wrist, a backpack, SCUBA equipment, a SCUBA gas tank, or a closed circuit re breather worn by the individual.

6. The method according to claim 1, further comprising limiting the conduction of the direct current through the associated insulating layer of material below 1 pA.

7. The method according to claim 1, wherein measuring the bioelectric signals is performed while each capacitive-type sensor is completely underwater.

8. The method according to claim 1, wherein measuring the bioelectric signals is performed after partially covering each capacitive-type sensor with the housing, the housing including a mechanical or structural enclosure that protects each capacitive-type sensor from water.

9. The method according to claim 1, wherein measuring the bioelectric signals is performed after covering each capacitive-type sensor with a hydrophobic coating located on the associated insulating layer of material.

10. The method according to claim 1, wherein the individual is a living organism.

11. The method according to claim 10, wherein measuring the bioelectric signals includes measuring bioelectric signals generated by organs of the living organism including the following types of signals: electrocardiogram (ECG), electroencephalogram (EEG), electrooculogram (EOG), electromyogram (EMG), or combinations thereof.

12. The method according to claim 1, further comprising injecting an excitation current or voltage into the individual to produce a voltage constituting the bioelectric signal.

13. A sensor system for measuring a bioelectric signal of an individual having skin, said system comprising:
a plurality of sensors, at least two of the plurality of sensors being constituted by a capacitive-type sensors, wherein each capacitive-type sensor has an associated insulated layer of material and is configured to be placed at a distance from the individual, to form a gap between the associated insulated layer of material and the skin so as to prevent conduction of direct current between the skin of the individual and the capacitive-type sensor, and to measure the bioelectric signal of the individual when the capacitive-type sensor is partially underwater with at least some water present between the individual's skin and the associated insulating layer of the capacitive-type sensor, wherein each capacitive-type sensor has an input electrode covered with the associated insulated layer of material preventing the conduction of the direct current, a first stage amplifier connected to the input electrode, a conductive housing encasing the input electrode, a wire, and circuitry configured to provide a guard voltage to the conductive housing, so that said conductive housing is configured to receive the guard voltage connected to an active guard driven at a guard voltage for protecting the input electrode from electromagnetic interference.

14. The system according to claim 13, wherein one of the capacitive-type sensors is completely underwater.

15. The system according to claim 13, wherein one of the capacitive-type sensors is an active capacitive-type sensor.

16. The system according to claim 13, where the plurality of sensors is mounted in a harness or holding device.

17. The system according to claim 13, wherein the plurality of sensors is embedded into a wet or dry diving suit.

18. The system according to claim 16, wherein the harness or holding structure keeps the plurality of sensors spaced from the skin of the individual.

19. The system according to claim 13, further comprising an injection electrode adapted to inject a current or voltage into a body of the individual to generate the bioelectric signal as a resulting voltage in the individual, whereby the resulting voltage of the individual is configured to be measured underwater; the system further comprising an electronics module including a processor for analyzing the resulting voltage to calculate an impedance value of the body of the individual.

20. The system according to claim 13, each capacitive-type sensor is partially covered with the housing, the housing including a mechanical or structural enclosure that protects each capacitive-type sensor from water.

21. The system according to claim 13, wherein each capacitive-type sensor is covered with a hydrophobic coating located on the associated insulating layer of material.

22. The system according to claim 13, wherein each capacitive-type sensor is also configured to measure the bioelectric signal of the individual while the sensor is not underwater and with no water present between the individual's skin and the insulating layer of each capacitive type sensor.

\* \* \* \* \*